United States Patent [19]

Abidi et al.

[11] Patent Number: 4,765,978
[45] Date of Patent: Aug. 23, 1988

[54] NOVEL VAGINAL SUPPOSITORY

[75] Inventors: Syed E. Abidi, Sewaren, N.J.; Joel A. Sequeira, New York, N.Y.

[73] Assignee: Schering Corporation, Kenilworth, N.J.

[21] Appl. No.: 942,563

[22] Filed: Dec. 16, 1986

[51] Int. Cl.$^4$ .................. A61K 31/79; A61K 31/415; A61K 9/02
[52] U.S. Cl. ..................................... 424/80; 424/433; 514/397; 514/967
[58] Field of Search ....................... 514/967, 399, 397; 424/DIG. 15, 80, 83, 433

[56] References Cited

U.S. PATENT DOCUMENTS 4,352,808 10/1982 Rane et al. .......................... 514/314
4,542,020 9/1985 Jackson et al. ....................... 514/31

OTHER PUBLICATIONS

Mycelex-G 500 mg Vaginal Tablet, Miles Pharm., 1980, package insert.
*The Theory and Practice of Industrial Pharmacy*, 2nd Ed., 1976, Lachman et al., Chap. 8 "Suppositories," pp. 245–273.

Primary Examiner—Albert T. Meyers
Assistant Examiner—Richard Kearse
Attorney, Agent, or Firm—John J. Maitner; Stephen I. Miller; James R. Nelson

[57] ABSTRACT

An antifungal vaginal suppository is disclosed comprising cis-2-(1H-imidazolylmethyl)-3-(2',6'-difluorobenzyloxy)-2,3-dihydro-5-fluorobenzo[b]thiophene in a suppository base containing biocompatible polymers, a surfactant and an absorbent in a vegetable oil phase.

10 Claims, No Drawings

NOVEL VAGINAL SUPPOSITORY

The present invention relates to a composition for treating fungal infections. More specifically, it relates to novel antifungal vaginal suppositories which contain cis-2-(1H-imidazolylmethyl)-3-(2',6'-difluorobenzyloxy)-2,3-dihydro-5-fluorobenzo[b]thiophene as the antifungal agent, in a suppository base containing biocompatible polymers, a surfactant and an absorbent in a vegetable oil phase. The suppositories are substantive and provide a prolonged duration of effectiveness.

U.S. Pat. No. 4,352,808 discloses 3-aralkyloxy-2,3-dihydro-2-(1H-imidazolylmethyl)benzo[b]thiophene compounds having antifungal and antibacterial activity. The compound utilized in the present invention, cis-2-(1H-imidazolylmethyl)-3-(2',6'-difluorobenzyloxy)-2,3-dihydro-5-fluorobenzo[b]thiophene, can be prepared as described in Example 1 of copending application of Rane et al. for "2-Azolyl-methyl-3- difluorobenzyloxy-2,3-dihydrofluorobenzo[b]thiophene antifungal compounds and method of using same", Ser. No. 684,872, filed Dec. 21, 1984, now U.S. Pat. No. 4,695,579 of common assignee as the instant application.

For treatment of vaginal infections, suppositories provide an effective mode for administration of a therapeutic agent. Although suppositories have attained some success, they have some disadvantages. Most of the current commercial vaginal suppositories, either melt or dissolve in the vaginal tract into an oily or aqueous liquid. This resulting liquid in turn tends to leak out or is expelled out of the vaginal cavity resulting either in soiled clothing and/or inferior efficacy. Accordingly, it is an object of the present invention to provide an effective antifungal suppository formulation which overcomes the noted disadvantages associated with the prior art suppositories.

In accordance with the present invention, an antifungal suppository formulation is provided which is substantive to the vaginal mucosa and delivers the drug over a prolonged period of time. The antifungal suppository formulation of the invention is formed of an antifungally effective amount of cis-2-(1H-imidazolylmethyl)-3-(2',6'-difluorobenzyloxy)-2,3-dihydro-5-fluorobenzo[b]thiophene in a suppository base containing biocompatible polymers, a surfactant and an absorbent in a vegetable oil phase.

The suppository formulation of the invention is useful in treating vaginal fungus infections in mammalian species, such as humans, cats, dogs and the like. The suppository formulation is easily inserted into the vaginal cavity and slowly melts at body temperature soon after insertion. Upon melting, the suppository turns into a gel/cream like consistency which adheres to the vaginal membrane providing prolonged duration of effectiveness.

The vaginal suppository formulation of the invention includes an antifungally effective amount of the drug, cis-2'(1H-imidazolylmethyl)-3-(2',6'-difluorobenzyloxy)-2,3-dihydro-5-fluorobenzo[b]thiophene. The amount of drug present in the suppository of the invention can vary from 2 to 20 percent by weight of the total weight of the suppository. The preferred amount of drug is approximately 18 percent by weight. The suppository of the present invention provides a long duration release period of from 8-12 hours in an animal screen.

The biocompatible polymer component of the suppository formulation comprises a combination of polyethylene and polyvinylpyrrolidione. The polyethylene utilized in the invention is a homopolymer of polyethylene. Examples of homopolymers of polyethylene that are useful in this invention are polyethylene waxes having Mettler Drop Point of from 102° C. to 117° C., density 0.91–0.94 g/cc and viscosity at 140° C. Brookfield 180–450 cps and are available from Allied Corp., Morristown, N.J., as A-C Polyethylene 6A, 9A and 617A.

The polyvinylpyrrolidione utilized in the invention is a synthetic water soluble polymer consisting essentially of linear 1-vinyl-2-pyrrolidone groups in which the degree of polymerization results in polymers of various molecular weights. It is characterized by its viscosity in aqueous solution; relative to that of water, expressed as a K-value, ranging from 10 to 95. Examples of polyvinylpyrrolidinones useful in the formulation of this invention are Povidone, USP K29/32 having an average molecular weight of about 40,000, PVP K-30, PVP K-60, PVP K-90, all supplied by GAF Corp., Wayne, N.J.

The total amount of biocompatible polymer that may be present in the suppository formulation of the invention is from 1 to 6 percent by weight of the total weight of the suppository. The preferred amount of biocompatible polymers is approximately 4 percent by weight. Of the total amount of biocompatible polymer present in the suppository, 1 to 5 percent by weight may be polyethylene and 0.2 to 1.0 percent by weight may be polyvinylpyrrolidione. In a preferred embodiment of the invention there is approximately 3.5 percent by weight of biocompatible polymers in the suppository and of the total amount of biocompatible polymers present 3.0 percent by weight is polyethylene and 0.5 percent is polyvinylpyrrolidione.

The vegetable oil phase suitable for use in the suppository formulation of the invention comprises hydrogenated vegetable oils, for example triglycerides derived from coconut oil and palm kernel oil; triglycerides of $C_{12}$–$C_{18}$ fatty acids, and the like. It has been found advantageous to utilize a mixture of triglycerides derived from coconut oil and palm kernel oil in combination with triglycerides of $C_{12}$–$C_{18}$ fatty acids. Examples of triglycerides derived from lauric based fats such as coconut oil and palm kernel oil useful in this invention include: Wecobee S and Wecobee FS available from PVO International Inc. Examples of triglycerides of $C_{12}$–$C_{18}$ fatty acids useful in this invention include: Witepsol H15, Witepsol S55 and Witepsol W35 available from Dynamit-Nobel A.G. An hydrogenated triglyceride with fatty alcohols and emulsifiers designated Suppostal-Es, available from Mediforma, Milan, Italy, can also be utilized in preparing the suppository formulation of the invention.

The amount of the vegetable oil phase that may be present in the suppository of the invention is from 60 to 80 percent by weight of the total weight of the suppository. The preferred amount of vegetable oil phase is approximately 75 percent by weight of the total amount of the suppository. Of the total amount of vegetable oil phase present in the suppository, 10 to 50 percent by weight may be a triglyceride derived from coconut oil and palm kernel oil and 50 to 80 percent by weight of triglycerides of $C_{12}$–$C_{18}$ fatty acids. In a preferred embodiment of the invention there is approximately 25 percent by weight of triglycerides derived from coconut oil and palm kernel oil and approximately 75 percent of triglycerides of $C_{12}$–$C_{18}$ fatty acids.

Incorporation of a water absorbent in the suppository formulation of the invention aids in forming a cream-like consistency material after the suppository melts in the vagina. An example of a water absorbent that may be utilized in the formulation is hydrated silica, such as Syloid 244 and Syloid 244P available from Davidson Chemical Division of W.R. Grace & Co. The amount of absorbent present in the formulation is 1.0 to 3.0 percent by weight, and preferably 1.75 percent by weight of the suopository.

Addition of surfactant to the suppository formulation of the invention assits in dispersion of the antifungal agent and biocompatible polymers about the vaginal cavity. Examples of surfactants that may be used in the formulation are glyceryl ricinoleate, Softigen 701 available from Dynamit-Nobel A.G., glyceryl oleate diluted in propylene glycol, Arlacel 186 available from ICI Americas Inc., Wilmington, Del. The amount of surfactant present in the formulation is 3 to 6 percent by weight, and preferably 3.5 percent by weight of the suppository.

In addition to the above noted components of a composition of this invention, the composition can be further modified by including an antioxidant. Examples of antioxidants that may be incorporated in the composition are conventional alkylated hydroxy compounds such as butylated hydroxytoluene (BHT) or butylated hydroxyanisole (BHA). The preferred antioxidant is butylated hydroxytoluene. The amount of antioxidant present in the formulation is 0 to 1 percent by weight.

The suppository formulation of the invention may be prepared by employing conventional suppository formulating techniques. In a preferred method, heat and melt the hydrogenated vegetable oils, the polyethylene and silica gel in a suitable compounding vessel. Then charge the polyvinylpyrrolidone, the drug and the surfactant to the melted suppository base. Mix until homogenous and while maintaining the temperature between 40°-50° C., the mass is poured into appropriate molds to form suppositories upon cooling.

The following formulation examples illustrate the suppository compositions of the invention. It will be apparent to those skilled in the art that many modifications thereof may be practical without departing from the purpose and intent of this disclosure. The definition of components whose chemical composition is not immediately clear from the name used may be found in the CTFA Cosmetic Ingredients Dictionary, 3rd Edition, published by Cosmetic Toiletry and Fragrance Association, Inc., Washington, D.C.

EXAMPLE 1

An antifungal suppository formulation in accordance with the present invention having the following composition was prepared as described below. The term "Drug" as used herein refers to cis-2-(1H-imidazolylmethyl)-3-(2',6'-difluorobenzyloxy)-2,3-dihydro-5-fluorobenzo[b]thiophene.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl ricinoleate | 104.0 |
| Witepsol S-55 | 582.0 |
| Wecobee FS | 1,745.2 |

The suppositories are prepared in the following manner: Heat and melt the hydrogenated vegetable oil (Witepsol and Wecobee), polyethylene and hydrated silica in a suitable compounding vessel. Then add the polyvinylpyrrolidione, the Drug and surfactant. Mix until homogeneous while maintaining the temperature between 40°-50° C. Then pour the mass into appropriate molds to form suppositories upon cooling.

EXAMPLE 2

An antifungal suppository of the following composition was prepared following a similar procedure to that described in Example 1.

| Ingredient | Amount (mg/suppository) |
| --- | --- |
| Drug | 600.0 |
| Polyethylene | 104 0 |
| Polyvinylpyrrolidione | 13.0 |
| Hydrated silica 244 | 52.0 |
| Glyceryl ricinoleate | 104.0 |
| Witepsol H-15 | 582.0 |
| Wecobee S | 1745.0 |

EXAMPLE 3

An antifungal suppository of the following composition was prepared following a similar procedure to that described in Example 1.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl oleate and propylene glycol | 104.0 |
| Witepsol W-35 | 582.0 |
| Suppostal Es | 1745.0 |

EXAMPLE 4

An antifungal suppository of the following composition was prepared following a similar procedure to that described in Example 1.

| Ingredient | Amount (mg/suppository) |
| --- | --- |
| Drug | 256.00 |
| Polyethylene | 117 76 |
| Polyvinylpyrrolidione | 14.72 |
| Hydrated silica | 58.88 |
| Glyceryl ricinoleate | 117.76 |
| Witepsol W-35 | 658.72 |
| Wecobee FS | 1976.16 |

EXAMPLE 5

An antifungal suppository of the following composition was prepared following a similar procedure to that described in Example 1.

| Ingredient | Amount (mg/suppository) |
| --- | --- |
| Drug | 64.00 |
| Polyethylene | 125.44 |
| Polyvinylpyrrolidione | 15.68 |
| Hydrated silica | 62.72 |
| Glyceryl ricinoleate | 125.44 |
| Witepsol S-55 | 701.68 |
| Wecobee FS | 2105.04 |

EXAMPLE 6

An antifungal suppository of the following composition was prepared following a similar procedure to that described in Example 1.

| Ingredient | Amount (mg/suppository) |
| --- | --- |
| Drug | 384.00 |
| Polyethylene | 112.64 |
| Polyvinylpyrrolidione | 14.08 |
| Hydrated silica | 56.32 |
| Glyceryl ricinoleate | 112.64 |
| Witepsol S-55 | 630.08 |
| Wecobee S | 1890.24 |

EXAMPLE 7

An antifungal suppository of the following composition was prepared following a similar procedure to that described in Example 1.

| Ingredient | Amount (mg/suppository) |
| --- | --- |
| Drug | 640.0 |
| Polyethylene | 102.4 |
| Polyvinylpyrrolidione | 12.8 |
| Hydrated silica | 51.2 |
| Glyceryl ricinoleate | 102.4 |
| Witepsol H-15 | 572.8 |
| Wecobee FS | 1718.4 |

EXAMPLE 8

An antifungal suppository of the following composition was prepared following a similar procedure to that described in Example 1.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl ricinoleate | 104.0 |
| Butylated hydroxytoluene | 50.0 |
| Witepsol H-15 | 582.0 |
| Wecobee FS | 1695.0 |

EXAMPLE 9

An antifungal suppository of the following composition was prepared following a similar procedure to that described in Example 1.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl ricinoleate | 104.0 |
| Butylated hydroxytoluene | 100.0 |
| Witepsol H-15 | 582.0 |
| Wecobee S | 1645.0 |

EXAMPLE 10

An antifungal suppository of the following composition was prepared following a similar procedure to that described in Example 1.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl oleate and propylene glycol | 104.0 |
| Butylated hydroxytoluene | 50.0 |
| Witepsol S-55 | 582.0 |
| Wecobee FS | 1995.0 |

EXAMPLE 11

An antifungal suppository of the following composition was prepared following a similar procedure to that described in Example 1.

| Ingredient | Amount (mg/suppository) |
| --- | --- |
| Drug | 600.0 |
| Polyethylene | 104.0 |
| Polyvinylpyrrolidione | 13.0 |
| Hydrated silica | 52.0 |
| Glyceryl oleate and propylene glycol | 104.0 |
| Butylated hydroxytoluene | 100.0 |
| Witepsol W-35 | 582.0 |
| Suppostal Es | 1645.0 |

The suppositories of the composition described in Example 1 were tested for their effectiveness in treating *Candida albicans* infection in hamsters. Groups of female outbred hamsters (Charles River) weighing 100–120 grams were used in testing.

The infecting organism, *C. albicans* (C-60) was grown on Sabouraud Dextrose Agar slants for 24 to 28 hours at 28° C. Cells were washed off the slants with broth to obtain a suspension of approximate $1 \times 10^8$ cells/ml.

On the first day of the study, the vagina was swabbed with a dry cotton swab to remove any mucus and to induce a slight irritation. The suspension of *C. albicans* (0.05 ml) was introduced into the vagina on three successive days (days 1, 2 and 3) using a syringe equipped with a blunt needle. Two days after infection (day 5) samples were obtained for culture by inserting a sterile cotton swabs into the vagina and then inserting these swabs into tubes containing a prepared culture broth [Saboarand Dextrose Broth containing cycloheximide 0.45 g/l and chloramphenicol 0.1 g/l]. All animals that failed to have positive culture were eliminated from the test prior to treatment.

Suppositories (drug treatment) were inserted into the vagina 4 days after completion of infection (day 7). Vaginal samples were obtained after 10 days of treatment using a sterile cotton swab. The swabs were placed into 10 ml of 0.9% saline containing cycloheximide (0.45 g/l) and chloramphenicol (0.1 g/l) and then vigorously agitated to dislodge the vaginal sample. A 2 ml aliquot of each sample was then passed through a 0.45 mm Millipore filter. Following a saline rinse of the filters, the filters were placed in Mycosal Agar plates and incubated at 37° C. After 48 hours the number of *C. albicans* colonies on the filters were counted.

Results. Suppositories of the present invention were compared with suppositories containing 2%, 5% and 10% miconazole. The percentage of hamsters cured as indicated by the 10 day cultures (Table 1) indicate that the antifungal suppositories of the present invention are superior to suppositories containing miconazole.

TABLE 1

In Vivo Activity of Drug and
Miconazole in Various Formulations
Against *C. albicans* Infection in Hamsters
Treatment as a Single Suppository Insert with Cultures
After 10 Days

| Formulation | Percentage of Hamsters Cured (50 Colonies/Hamster) | |
|---|---|---|
| | Conc. (%) | Day 10 |
| Drug | 2 | 75 |
| Drug | 5 | 91 |
| Drug | 10 | 91 |
| Vehicle | — | 50 |
| Miconazole nitrate | 2 | 42 |
| Miconazole nitrate | 5 | 45 |
| Miconazole nitrate | 10 | 45 |

What is claimed is:

1. A vaginal suppository comprising 2 to 20% by weight of cis-2-(1H-imidazolylmethyl)-3-(2',6'-difluorobenzyloxy)-2,3-dihydro-5-fluorobenzo[b]thiophene, 1 to 5% by weight of polyethylene, 0.2 to 1% by weight of polyvinylpyrrolidone, 3 to 6% by weight of surfactant, 1 to 3% by weight of absorbent, 60 to 80% by weight of vegetable oil phase and 0 to 1% by weight of antioxidant.

2. The suppository according to claim 1 comprising 2 to 20% by weight of cis-2-(1H-imidazolylmethyl)-3(2',6'-difluorbenzyloxy)-2,3-dihydro-5-fluorobenzo[b]thiophene, 1 to 5% by weight of polyethylene, 0.2 to 1.0% by weight of polyvinylpyrrolidone, 1 to 3% by weight of hydrated silica, 3 to 6% by weight of glyceryl ricinoleate, 60 to 80% by weight of vegetable oil phase and 0 to 1% by weight of antioxidant selected from the group consisting of butylated hydroxyanisol and butylated hydroxytoluene.

3. The suppository according to claim 2 wherein the vegetable oil phase comprises 10 to 50% by weight triglycerides derived from coconut oil and palm kernel oil and 50 to 80% by weight triglycerides of $C_{12}$–$C_{18}$ fatty acids.

4. The suppository according to claim 3 wherein the vegetable oil phase comprises 25% by weight triglycerides derived from coconut oil and palm kernel oil and 75% by weight triglycerides of $C_{12}$–$C_{18}$ fatty acids.

5. A vaginal suppository comprising 600 mg cis-2-(1H-imidazolylmethyl)-3-(2',6'-difluorobenzyloxy)-2,3-dihydro-5-fluorobenzo[b]thiophene, 104 mg polyethylene, 13 mg polyvinylpyrrolidione, 52 mg hydrated silica, 104 mg glyceryl ricinoleate, 582 mg Witepsol S-55 and 1,745.2 mg Wecobee FS.

6. A method of treating vaginal fungal infections comprising administering to the vaginal cavity a suppository in accordance with claim 1.

7. A method of treating vaginal fungal infections comprising administering to the vaginal cavity a suppository in accordance with claim 2.

8. A method of treating vaginal fungal infections comprising administering to the vaginal cavity a suppository in accordance with claim 3.

9. A method of treating vaginal fungal infections comprising administering to the vaginal cavity a suppository in accordance with claim 4.

10. A method of treating vaginal fungal infections comprising administering to the vaginal cavity a suppository in accordance with claim 5.

* * * * *